(12) United States Patent
Cappa et al.

(10) Patent No.: US 6,694,184 B2
(45) Date of Patent: Feb. 17, 2004

(54) SHIELDED PERMANENT MAGNET ACTIVATOR FOR IMPLANTED CARDIAC DEVICES

(75) Inventors: Armando M. Cappa, Granada Hills, CA (US); J. Kelly Fox, Valencia, CA (US); Paul A. Levine, Newhall, CA (US); Matthew Whitlock, Sherman Oaks, CA (US); James B. Hamilton, Canyon Country, CA (US)

(73) Assignee: Pacesetter, Inc., Sylmar, CA (US)

( * ) Notice: Subject to any disclaimer, the term of this patent is extended or adjusted under 35 U.S.C. 154(b) by 307 days.

(21) Appl. No.: 09/757,143

(22) Filed: Jan. 9, 2001

(65) Prior Publication Data

US 2002/0091413 A1 Jul. 11, 2002

(51) Int. Cl.$^7$ ............................................. A61B 19/02
(52) U.S. Cl. ............................ 607/2; 128/899; 607/31; 206/818
(58) Field of Search .................. 607/60, 31, 1, 607/30, 63, 2, 32; 600/9, 15, 7; 128/899; 224/183; 335/205; 446/242

(56) References Cited

U.S. PATENT DOCUMENTS

| | | | | |
|---|---|---|---|---|
| D307,745 S | | 5/1990 | Adams | D13/183 |
| 5,002,068 A | * | 3/1991 | Provell | 128/845 |
| 5,128,643 A | * | 7/1992 | Newman | 335/301 |
| 6,082,367 A | | 7/2000 | Greeninger et al. | 128/899 |
| 6,128,526 A | | 10/2000 | Stadler et al. | 600/517 |
| 6,488,615 B1 | * | 12/2002 | Mitchiner et al. | 600/9 |

* cited by examiner

*Primary Examiner*—Kennedy Schaetzle

(57) ABSTRACT

A method and assembly for selectively actuating features of implanted medical devices with a magneto-static field. The method includes selectively exposing the implanted device to a static magnetic field source, selectively shielding the magnetic field source, and distancing the shielded magnetic field source from the medical device. One version of the assembly includes a permanent magnet and a displaceable shield assembly that shields the magnetic field generated by the magnet in one configuration and is displaceable to a second configuration wherein the magnetic field is at least partially exposed. In another version, the assembly is an electromagnet that can be selectively activated and deactivated. The electromagnet generates minimal magnet field when it is off.

22 Claims, 6 Drawing Sheets

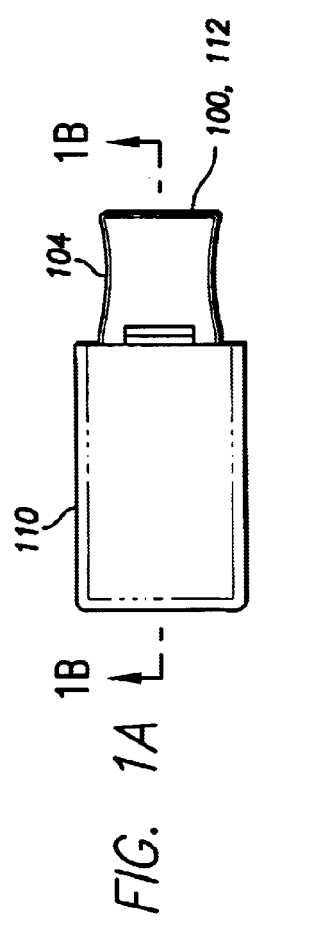
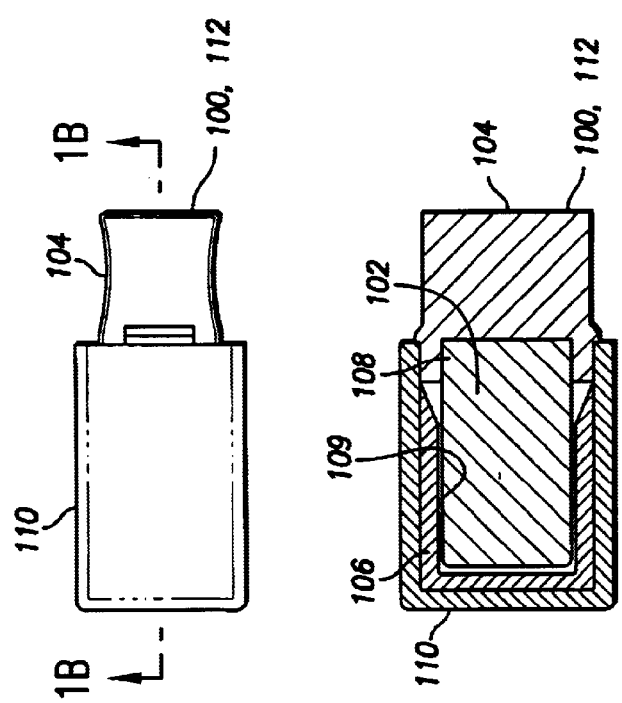
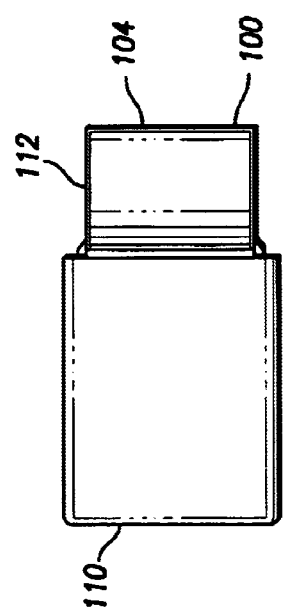
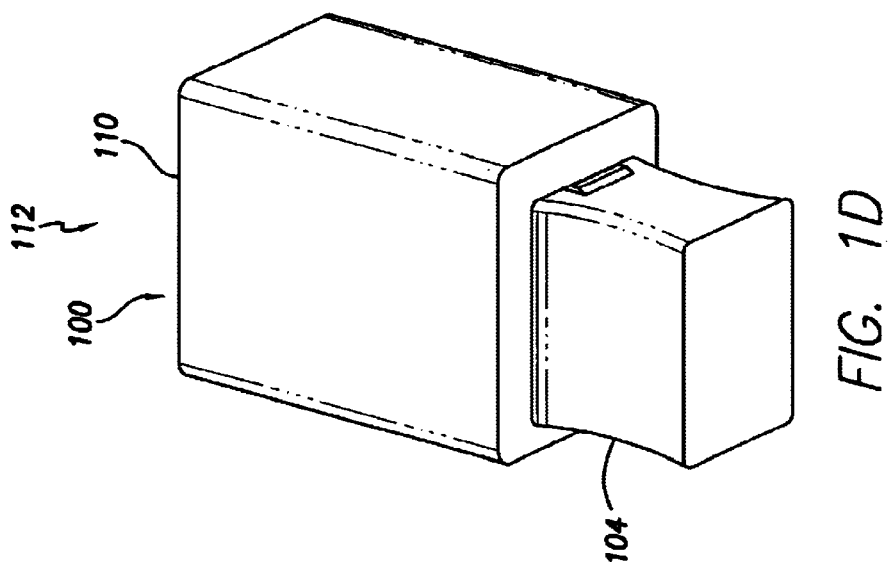
FIG. 1A
FIG. 1B
FIG. 1C
FIG. 1D

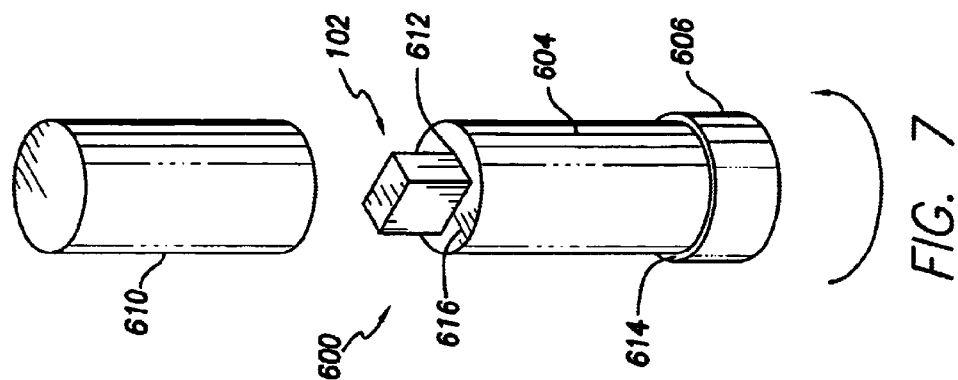
FIG. 7
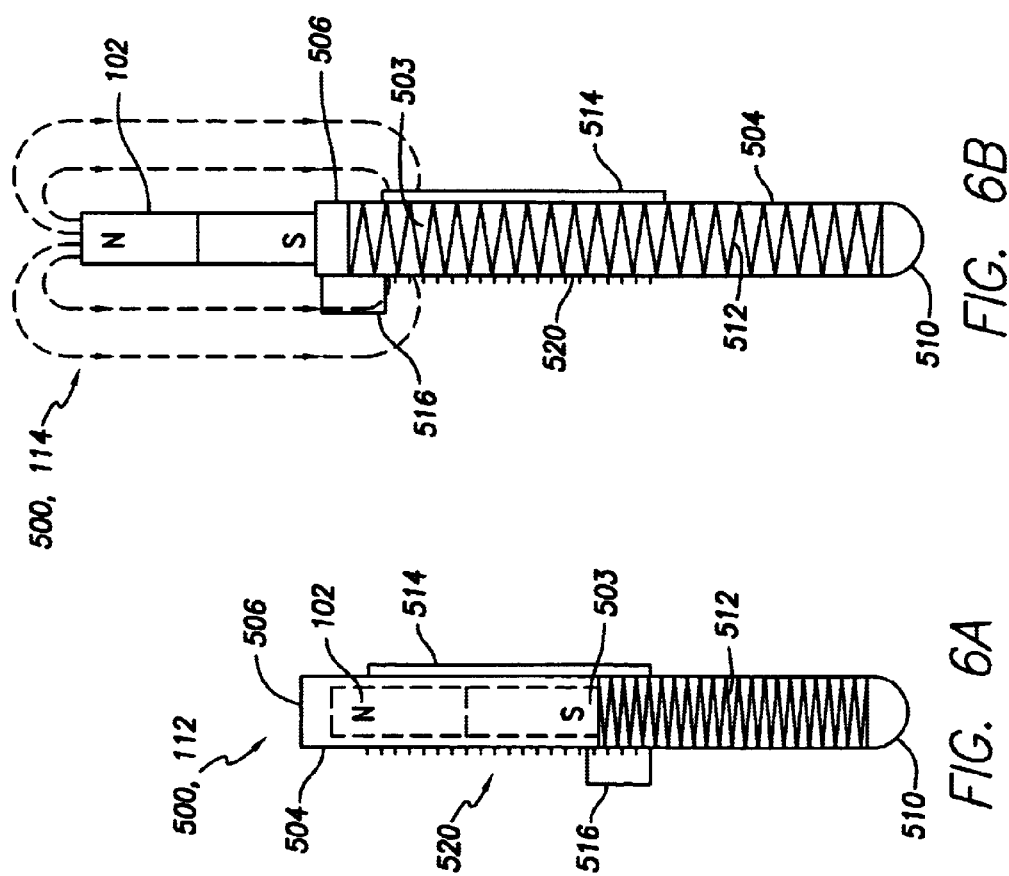
FIG. 6B
FIG. 6A

SHIELDED PERMANENT MAGNET ACTIVATOR FOR IMPLANTED CARDIAC DEVICES

FIELD OF THE INVENTION

The present invention relates to the field of implantable cardiac devices and, in particular, to a small permanent magnet provided with a displaceable, conformal magneto-static shield to inhibit unintentional exposure of the magnetic field that is suitable for carrying on the person.

BACKGROUND OF THE INVENTION

Cardiac devices are known assemblies implanted in patients to monitor the heart and provide therapeutic stimuli to treat a variety of arrhythmias. Many of these devices also have features that may be selectively activated by exposure to a magneto-static field. Typically, these devices include well-known reed switches that can be closed by exposure to a magnetic field of a given threshold value. A typical use of a magnetically activated reed switch in an implanted cardiac device is to enable a telemetry circuit within the device so that data indicative of the function of the patient's heart, as it is sensed by the implanted cardiac stimulation device, as well as data indicative of the function of the implanted device can be telemetered to an external programmer. This data can be reviewed by a treating medical professional. The advantage of using a magnetically activated switch in this circumstance is that it permits the selective activation of a particular function of the device that is implanted within the patient in a simple, non-invasive manner.

Magneto-static fields are chosen to activate these selectable features for several reasons. A patient is not likely to encounter strong magneto-static fields (>0.5 Gauss) inadvertently. Magneto-static fields pass relatively readily through the body and thus to the implanted device. Magneto-static fields of reasonable strength have no known injurious effects on the human body. A small, high strength permanent magnet can be readily carried on the person and used by the patient to activate the selectable features of the cardiac device when desired.

However, several problems occur with carrying a permanent magnet on the person. If the magnet is inadvertently brought too close to the device, the selectable features of the device can be unintentionally activated. Also, strong magneto-static fields can irreparably scramble data stored on magnetic recording media. In fact, exposure to high gauss fields is a known manner of wiping magnetic recording media, such as computer diskettes, audio tapes and the like. Credit cards are also typically provided with magnetic strips with account holder information encoded therein and exposure to a permanent magnet can erase this information from the card.

An additional liability to permanent magnets carried on the person is that they are attracted to and can adhere to ferrous material. For example, a magnet carried in the person's pocket can be attracted and stick to a steel structure. It will be appreciated that a magnet, unexpectedly adhering to a steel railing on a stairway, for example, could induce a person to stumble and fall, possibly leading to injury. A permanent magnet would also be attracted to ferrous items such as keys, pocketknives, pens, and fingernail files that are often carried in a purse or pocket. A magnet could further attract and knock over steel objects such as cans, medical instruments, etc. as a person carrying a magnet walks by.

In addition, exposing certain materials, the most common of which are ferrous materials, to a magnetic field causes the materials so exposed to become magnetized themselves. Thus a steel key and key ring, for example, placed in proximity to a permanent magnet, would become partially magnetized themselves and would have similar characteristics to those of the original magnet.

A further difficulty that occurs with these magnets in connection with implantable cardiac devices is that the unshielded magnets are strong enough to result in inadvertent activation of the reed switches in an implanted device while the medical professional carrying the magnet is in the presence of the patient. This can result in undesired operation of the device resulting in undesired drain of limited battery resources. Moreover, the magnets are also strong enough that the magnets can affect the operation of external programmers that are used to evaluate the operation of the cardiac stimulation device implanted within the patient.

Unfortunately, while these magnets are necessary to permit remote activation of functions within the implanted cardiac stimulation device, there is no way to deactivate the magnets. Hence, the problems associated with carrying around magnets of sufficient strength to activate functions within an implanted cardiac stimulation device have not been readily addressed in the prior art.

From the foregoing it will be appreciated that there is an ongoing need for a small, permanent magnet that can be readily carried on a person to enable a person implanted with a cardiac stimulation device to employ the magnet to selectively activate certain features and functions of the implanted device. Moreover, there is still an ongoing need to develop a magnet device suitable for activation of magnetic switches in implanted cardiac devices that can also be shielded when the magnet device is not being used to avoid the difficulties associated with medical professionals carrying around powerful magnets.

SUMMARY OF THE INVENTION

The aforementioned needs are satisfied by the magnet device of the present invention which in one aspect is comprised of a magnet and a configurable container. The magnet can be exposed wherein it produces a magnetic field of a first strength sufficient to activate a magnetic switch within an implanted cardiac stimulation device to thereby induce the implanted cardiac stimulation device to perform a selected function. The magnet can also be shielded within the container such that the magnet produces a field of second strength that is sufficiently less than the first strength such that the magnet does not activate the magnetic switch within the implanted cardiac stimulation device.

Preferably, the container defines a high magnetic permeability path through which a substantial portion of the flux flows to thereby reduce the strength of the magnetic field outside the container. Preferably, the container is made of a material that has a high level of magnetic permeability. Magnetic permeability in the context of magnetic fields is analogous to electrical conductivity in the context of electrical current. Given alternative paths with high and low conductivity, electrical current will predominantly flow through the path with high conductivity (low resistance). In a similar manner, magnetic fields will predominantly pass through regions of high permeability in preference to regions of low permeability. Air and most common materials have relatively low permeabilities on the order of 1. However, materials such as iron and MuMetal® have permeabilities on the order of tens of thousands. Thus, in one embodiment, if the container has sufficient quantities of high permeability material that is placed about the permanent magnet, the magnetic field will predominately pass within the highly permeable path and thus reduce the magnetic field strength induced by the permanent magnet outside of the container. Advantageously, the high permeability material does not damage magnetic field strength, it is simply providing a more permeable path for the magnetic flux in the container material.

In one embodiment, the magnet device produces a magnetic field of at least 10 Gauss measured 7.6 cm from the magnet. When the magnet is shielded within the container, in this embodiment, the magnet produces a magnetic field of less than 2 Gauss measured 7.6 cm from the magnet.

The container can have a variety of different configurations. The magnet can be positioned within a container such that it can be removed from the container. The magnet can also be fixedly mounted within the container and a lid of the container can be removed or the magnet can be otherwise exposed to produce the larger magnetic field.

In another aspect, the magnetic device can include an electromagnet assembly for selectively activating features of an implanted cardiac stimulation device. In this aspect, the magnet device is electrically actuated to produce a stronger magnetic field having a magnetic field strength sufficient to activate a magnetic switch in an implanted device. When the device is not actuated, the magnetic field strength is low enough not to result in activation of the magnetic switches and also reduces the inconvenience of having a strong magnet in the presence of other metal objects.

The present invention therefore provides a mechanism that reduces the negative effects of magnetic fields emanating from magnets that are used to activate selected functions of implanted medical devices, such as implanted cardiac stimulation devices. These and other objects and advantages will be more apparent from the following discussion taken in conjunction with the accompanying drawings.

BRIEF DESCRIPTION OF THE DRAWINGS

Further features and advantages of the present invention may be more readily understood by reference to the following description taken in conjunction with the accompanying drawings, in which:

FIGS. 1A–1D illustrate in four views one embodiment of a shielded magnet assembly in a shielded configuration;

FIG. 6A illustrates an embodiment of a shielded magnet assembly in a shielded configuration;

FIG. 6B illustrates the shielded magnet assembly of FIG. 6A in an exposed configuration;

FIG. 7 illustrates a further embodiment of a shielded magnet assembly;

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 2:
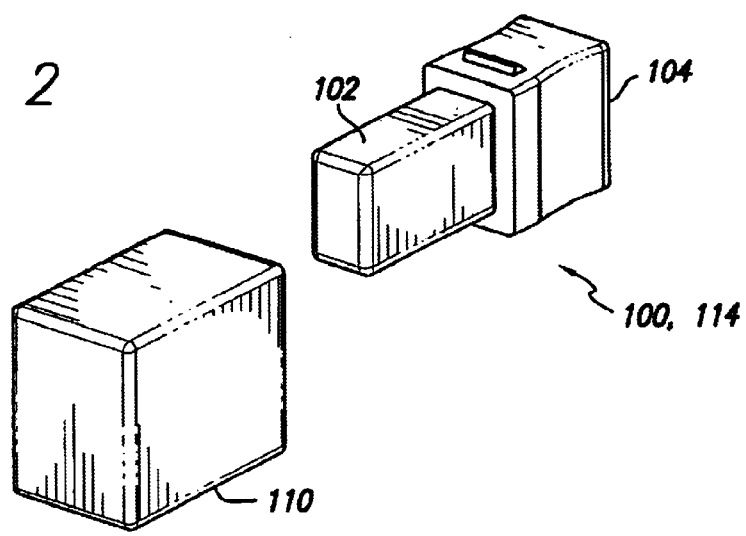
FIG. 2 illustrates the shielded magnet assembly of FIG. 1 in an exposed configuration.

FIGS. 1A–1D and 2 illustrate a shielded magnet assembly 100 in a shielded configuration 112 (FIGS. 1A–1D) and an exposed configuration 114 (FIG. 2). The shielded magnet assembly 100 comprises a permanent magnet 102 that is shielded in the shielded configuration 112 such that the magneto-static field developed by the magnet 102 is substantially directed within the shielded magnet assembly 100 such that a reduced magnetic field appears beyond the envelope of the assembly 100. A reduced magnetic field should be construed throughout this description that follows as meaning less than approximately 2 Gauss measured 7.6 cm in any direction from any exposed surface of the magnet 102.

More specifically, the permanent magnet 102 in the exposed configuration produces a magnetic field having a strength selected to activate a magnetic switch 117 (FIG. 9), such as a reed switch in an implanted cardiac stimulation device to thereby induce the implanted cardiac stimulation device to perform a pre-selected function. The magnetic field strength needed to activate the magnetic switch in an implanted device must be relatively strong as the magnetic switches are typically configured to only be activated by strong magnetic fields to reduce the risk of inadvertent triggering of the switches resulting from the patient being exposed to stray magnetic fields.

The magnet assembly 100 in the shielded configuration results in the magnet 102 being shielded sufficiently so that the magnetic field produced by the permanent magnet 102 outside of the envelope of the assembly 100 is low enough to reduce the inconvenience of carrying a strong magnet on the person of the treating medical professional. As will be described in greater detail below, the assembly 100 is preferably configured such that the permanent magnet does not produce a field outside of the envelope of the assembly 100 when the assembly is in the shielded configuration 112 that would be strong enough to activate the magnetic switches in the implanted device when the assembly 100 is positioned adjacent the skin of the patient proximate the implanted device.

As is illustrated in FIG. 2, the magnet 102 may also be exposed in the exposed configuration 114 such that the magnetic field developed by the magnet 102 is substantially unshielded on at least one pole to facilitate activating features and functions of an implanted cardiac device 116. The construction, use, and selectable features of the cardiac device 116 are well known to those of ordinary skill in the art.

The magnet 102, of this and all following embodiments, is made of a permanently magnetic material, such as Samarium-Cobalt, Neodymium-Iron-Boron, or other elements or alloys that are well known in the art. The size of the magnet 102 is chosen with respect to the intrinsic properties of the particular material chosen to develop a magnetic field of at least 10 Gauss as measured 7.6 cm from the surface of the magnet 102 of this and all following embodiments in the exposed configuration 114. The edges and corners of the magnet 102 are rounded or beveled in a known manner to avoid sharp and pointed edges which might otherwise cause injury to a user of the assembly 100.

The shielded magnet assembly 100 of this embodiment also comprises a magnet holder 104. The magnet holder 104 is a made of a material with a relatively high magnetic permeability, such as iron or an alloy of 77% Nickel, 14% Iron, 5% Copper, and 4% Molybdenum sold under the trademark MuMetal®. The magnet holder 104 defines a cavity 108. The cavity 108 in this embodiment is a generally rectangular opening extending into one end of the magnet holder 104. The size of the cavity 108 is chosen to closely conform to the size and shape of one end of the magnet 102. The magnet 102 is inserted into the cavity 108 so as to achieve a friction fit in a known manner. In an alternative embodiment, the magnet 102 is inserted into the cavity 108 and secured with an adhesive. The magnet holder 104, when attached to the magnet 102, provides a gripping surface for the user to manipulate the assembly 100.

The shielded magnet assembly also comprises a shield liner 106 and cover 110. The shield liner 106 is made of a material with a relatively high magnetic permeability, such as iron or an alloy of 77% Nickel, 14% Iron, 5% Copper, and 4% Molybdenum sold under the trademark MuMetal®. The cover 110 is made of a durable, smooth material such as plastic. The shield liner 106 and cover 110 are made such that the shield liner 106 fits tightly inside the cover 110 in a friction fit so as to fixedly attach the cover 110 to the shield liner 106.

The shield liner 106 defines a cavity 109. The cavity 109 is sized to closely conform to the contour of the magnet 102 so as to form a removable friction fit between the cavity 109 of the shield liner 106 and the magnet 102. The friction fit between the shield liner 106 and the magnet 102 retains the shield liner 106 and cover 110 in contact with the magnet 102 in the shielded configuration 112. However, the friction fit is such that the shield liner 106 and cover 110 can be readily removed from the magnet 102 to achieve the exposed configuration 114.

The shield liner 106 and magnet holder 104 are adapted such that, in the shielded configuration 112, the shield liner 106 and the magnet holder 104 are in continuous, adjacent contact. Since the magnet 102 is in physical contact with both the shield liner 106 and the magnet holder 104, the magnetic field developed by the magnet 102 will predominantly pass within the relatively high permeability material of the shield liner 106 and the magnet holder 104. As previously mentioned, the size, shape, and material of the shield liner 106 and the magnet holder 104 are chosen to limit the magnetic field beyond the envelope of the shield liner 106 and the magnet holder 104 to no more than 2 Gauss as measured 7.6 cm away.

Hence, the shield liner 106 and magnet holder 104 provide a high magnetic permeability path for the magnetic flux that is produced by the permanent magnet when it is in the shielded configuration 112. This path results in much of the magnetic flux generated by the magnet 102 being confined within the shield liner 106 thereby decreasing the strength of the magnetic field beyond the assembly 100.

The size and exact materials used to construct the magnet 102, magnet holder 104, and shield liner 106 are chosen to meet the shielded and exposed magnetic field requirements noted previously. It should be appreciated that the greater the intrinsic magnetic strength of the material used to construct the magnet 102 and the higher the magnetic permeability of the material used to construct the magnet holder 104 and the shield liner 106, the smaller the shielded magnet assembly 100 can be made. Smaller sizes of the assembly 100 improve convenience for a patient/user. Material choice and shape are chosen with other design constraints including material cost, availability, and ease of construction by one of skill in the art.

Figure 3:
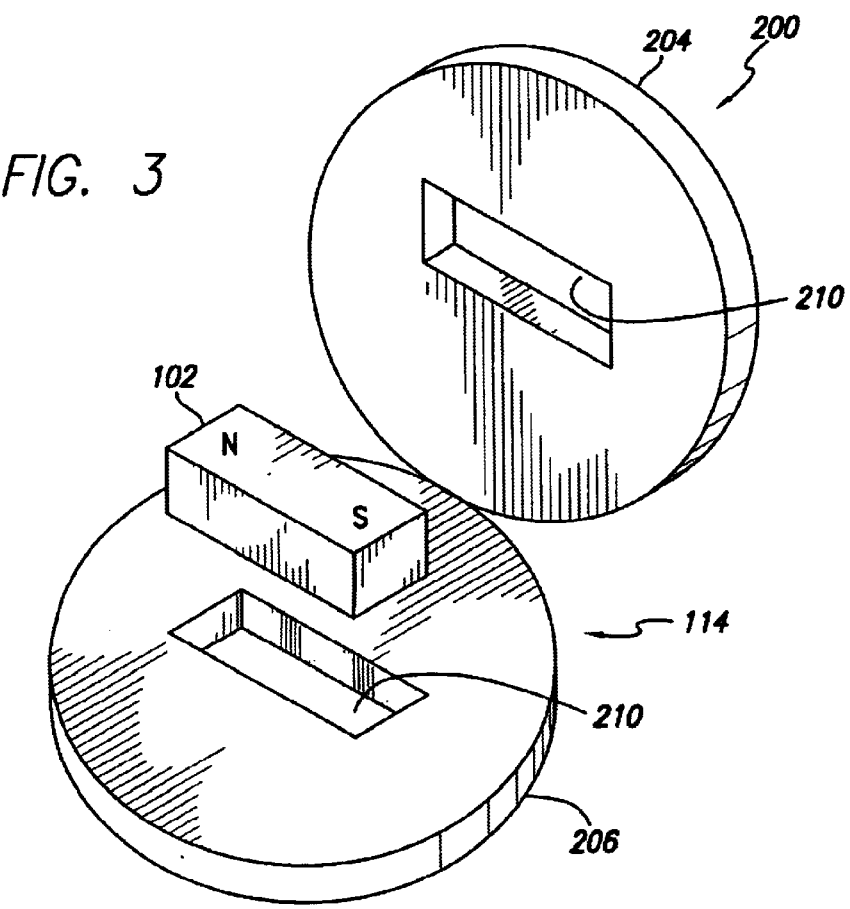
FIG. 3 illustrates an alternative embodiment of a shielded magnet assembly in an exposed configuration.

FIG. 3 illustrates an alternative embodiment of a shielded magnet assembly 200 in an exposed configuration 114. The shielded magnet assembly 200 of this embodiment comprises the magnet 102 substantially identical to the magnet 102 of the shielded magnet assembly 100 previously described. The shielded magnet assembly 200 also comprises a first 204 and a second 206 enclosure half. The first 204 and second 206 enclosure halves are made of a high permeability material, such as those previously described with respect to the magnet holder 104. The first and second enclosure halves 204, 206 thereby provide the high magnetic permeability path through which the magnetic flux flows when the assembly 200 is in the closed configuration to thereby reduce the strength of the magnetic field outside of the assembly 200. The first 204 and second 206 enclosure halves of this embodiment are substantially identical oblate members and are adapted to closely mate together.

The first 204 and second 206 enclosure halves of this embodiment are not attached, although, in alternative embodiments, the first 204 and second 206 enclosure halves are hingedly connected. The first 204 and second 206 enclosure halves each define a cavity 210. The cavity 210 in each of the first 204 and second 206 enclosure halves is configured to closely conform to the contour of the magnet 102. The first 204 and second 206 enclosure shells are each attached to the magnet 102, and thus held in adjacent contact with each other, by a friction fit with the magnet 102.

In an alternative embodiment, the first 204 and second 206 enclosure halves are held together in adjacent contact by hook and loop fastener secured and employed in a well known manner to adjacent faces of the first 204 and second 206 enclosure halves wherein the cavity 210 is sized with respect to the magnet 102 such that the magnet 102 is readily removable from both the first 204 and second 206 enclosure halves. In yet another alternative embodiment, the cavities 210 in the first 204 and second 206 enclosure halves are sized such that the magnet 102 fits tightly in a friction fit with one of the first 204 and second 206 enclosure halves and is thus fixedly attached to the one of the first 204 and second 206 enclosure halves. The cavity 210 in the other one of the first 204 and second 206 enclosure halves is sized such the magnet 102 and attached first 204 or second 206 enclosure half is readily removable from the other first 204 or second 206 enclosure half. The first 204 and second 206 enclosure halves, when positioned adjacent each other in the shielded configuration 112, shield the magnetic field developed by the magnet 102 in a similar manner to that previously described with respect to the shield liner 106 and magnet holder 104.

Figure 4:
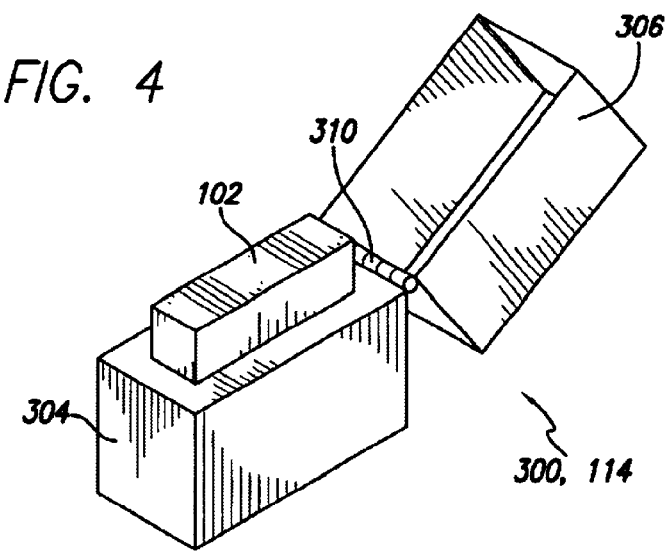
FIG. 4 illustrates another alternative embodiment of a shielded magnet assembly in an exposed configuration.

FIG. 4 illustrates another alternative embodiment of a shielded magnet assembly 300 in the exposed configuration 114. The shielded magnet assembly 300 of this embodiment comprises the magnet 102, a base member 304, and a cover 306. The base member 304 and cover 306 are made of a high permeability material, such as those previously described with respect to the magnet holder 104, and are hingedly attached in a well known manner. The hinged connection of the base member 304 and the cover 306 preferably includes a spring pre-load assembly 310 of a type well known in the art to bias the shielded magnet assembly 300 into either the shielded configuration 112 or the exposed configuration 114.

The exposed configuration 114 comprises distancing the cover 306 from the base member 304 as illustrated in FIG. 4. The shielded configuration 112 comprises rotating the cover 306 about the hinged connection to the base member 304 such that the cover 306 is adjacent and in continuous contact with the base member 304. The adjacent positioning of the cover 306 and the base member 304 in the shielded configuration 112 shields the magnetic field developed by the magnet 102 in a similar manner to that previously described with respect to the shield liner 106 and magnet holder 104.

Figure 5:
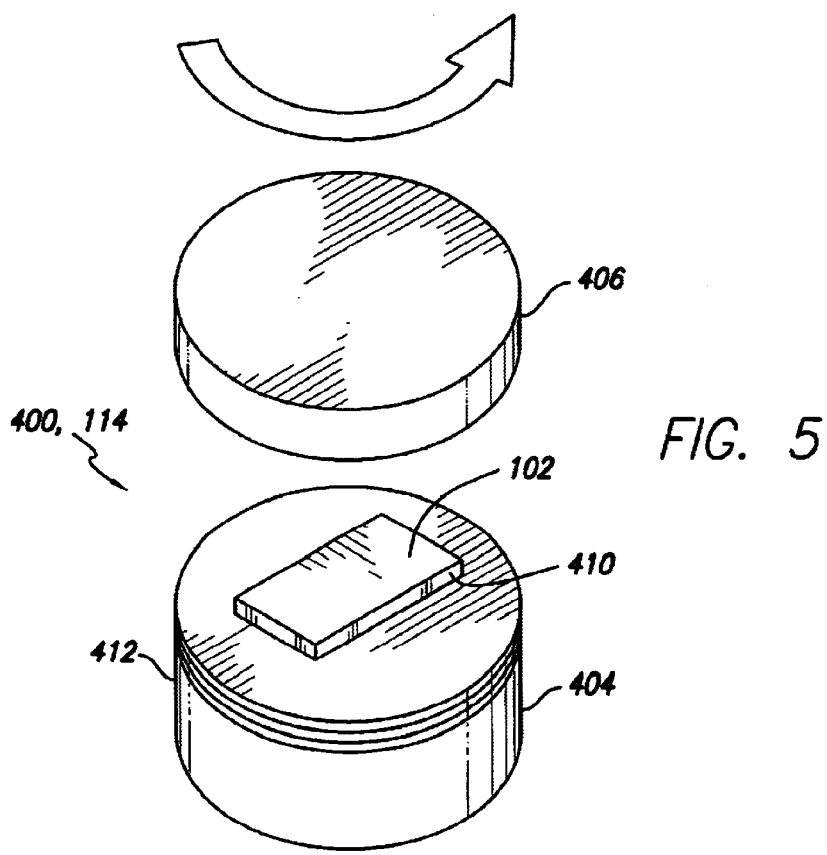
FIG. 5 illustrates yet another alternative embodiment of a shielded magnet assembly in an exposed configuration.

FIG. 5 illustrates yet another alternative embodiment of a shielded magnet assembly 400 in the exposed configuration 114. The shielded magnet assembly 400 of this embodiment comprises the magnet 102, a base member 404, and a lid 406. The base member 404 and lid 406 are made of a high permeability material, such as those previously described with respect to the magnet holder 104. The base member 404 is a generally cylindrical member and defines a cavity 410 adjacent a first end 412 of the base member 404. The cavity 410 is sized and configured to hold the magnet 102 in a friction fit such that the magnet 102 is at least partially exposed above the first end 412 of the base member 404. The base member 404 is provided with external threads of a known configuration about the circumference of the base member 404 adjacent the first end 412.

The lid 406 is a generally cylindrical, hollow member open on one end and closed on the opposite end. The open end of the lid 406 is provided with internal threads configured to mate with the threads of the base member 404.

The exposed configuration 114 of the shielded magnet assembly 400 comprises distancing the lid 406 from the base member 404 as illustrated in FIG. 5. In the exposed configuration 114, the base member 404 serves as a gripping surface for a user of the shielded magnet assembly 400. The shielded configuration 112 is achieved by threading the lid 406 onto the base member 404 in a known manner so as to bring the lid 406 and the base member 404 into adjacent, continuous contact along the respective threads provided on each. Thus, in similar manner to that previously described with the alternative embodiments of the shielded magnet assembly 100, 200, and 300, the magnetic field developed by the magnet 102 is substantially directed through the lid 406 and the base member 404 such that minimal magnetic field extends beyond the envelope of the shielded magnet assembly 400.

FIGS. 6A and 6B illustrate one more embodiment of a shielded magnet assembly 500 in the shielded configuration 112 (FIG. 6A) and the exposed configuration 114 (FIG. 6B). The shielded magnet assembly 500 comprises the magnet 102 and an enclosure 504. The enclosure 504 is a hollow, cylindrical elongate member approximately 1.25–1.5 cm in outer diameter and approximately 13–15 cm long. The enclosure 504 is open on a first end 506 and closed on a second end 510 opposite the first end 506. The enclosure 504 also defines a slot 520 extending along the major axis of the enclosure 504 from a point approximately midway between the first 506 and second 510 ends to the first end 506. The enclosure 504 is made of a high permeability material, such as those previously described with respect to the magnet holder 104. The magnet 102 of this embodiment is generally cylindrical and sized to conform closely to the interior of the enclosure 504 and to be approximately one-half the length of the enclosure 504, which, in this embodiment, corresponds to a magnet 102 of approximately 6–7 cm long.

The shielded magnet assembly 500 also comprises a spring 512. The spring 512 of this embodiment is a coil spring of a type well known in the art. The spring 512 is sized to closely fit within the interior of the enclosure 504. The spring 512 is positioned inside the enclosure 504 between the magnet 102 and the interior of the second end 510 of the enclosure 504. The spring 512 is further sized so as to have a free length of approximately 14 cm so as to apply a pre-load force on the magnet 102 when the magnet 102 is positioned so as to not protrude beyond the first end 506 of the enclosure 504 (i.e. in the shielded configuration 112) without coil-binding the spring 512.

In one embodiment, the magnet 102 is substantially of uniform diameter along its length and of such a diameter as to snuggly fit within the enclosure 504 so as to inhibit the magnet 102 inadvertently exiting the enclosure 504. In an alternative embodiment, the magnet 102 defines an annular region of greater diameter than the remainder of the magnet 102 thereby defining a flange adjacent a first end 503 of the magnet 102. The first end 506 of the enclosure 504 is slightly crimped after insertion of the spring 512 and magnet 102 into the interior of the enclosure 504 to thereby inhibit exiting of the magnet 102 and spring 512 from the enclosure 504.

The shielded magnet assembly 500 also comprises a clip 514. The clip 514 is an elongate member approximately 5 cm long and is made of an elastic, rigid material such as plastic or steel. The clip 514 is fixedly attached at a first end adjacent the first end 506 of the enclosure 504 so as to extend along the major axis of the enclosure 504 towards the second end 510 of the enclosure 504 and is positioned opposite the slot 520. The clip 514 is adapted such that a second end of the clip 514, opposite the first end of the clip 514, bears against the outside of the enclosure 504 in a spring-loaded fashion. The clip 514 facilitates securing the assembly 500 to a shirt pocket in a well understood manner.

The shielded magnet assembly 500 also comprises a thumbslide 516. The thumbslide 516 is a generally rectangular member and is made of a rigid, durable material such as plastic or steel. The thumbslide 516 is fixedly attached to the magnet 102 adjacent the first end 503 with a high strength adhesive so as to extend radially outward from the enclosure 504 through the slot 520. It should be noted that certain known methods of attaching a steel piece, in particular high temperature processes such as welding and brazing, are not appropriate methods for securing the thumbpiece 516 to the magnet 102 due to the possibility of exposing the magnet 102 to temperatures in excess of its Curie temperature and thereby reducing the magnetic field developed by the magnet 102. The thumbslide 516 facilitates extending and retracting the magnet 102 within the enclosure 504 in a well understood manner.

The shielded configuration 112 is achieved by manipulating the thumbslide 516 so as to draw the attached magnet 102 within the interior of the enclosure 504. When the magnet 102 is positioned within the enclosure 504, the magnetic field developed by the magnet 102 will substantially pass within the material of the enclosure 504 such that a reduced magnetic field appears beyond the envelope of the enclosure 504. The exposed configuration 114 is achieved by manipulating the thumbslide 516 to extend the magnet 102 beyond the first end 506 of the enclosure 504. In the exposed configuration 114, the magnetic field developed by the magnet 102 is exposed on a second end opposite the first end 503.

FIG. 7 illustrates yet even one more embodiment of a shielded magnet assembly 600. The shielded magnet assembly 600 of this embodiment comprises the magnet 102, an enclosure body 604, a knob 606, and a cap 610. The magnet 102 of this embodiment is a generally rectangular elongate member and is provided with internal, female threads (obscured from view) extending along the major central axis of the magnet 102. The enclosure body 604 is a elongate member of cylindrical outer contour and with a rectangular cavity 612 configured so as to allow the magnet 102 to freely move back and forth axially within the cavity 612 and further configured to inhibit rotation of the magnet 102 within the cavity 612. The enclosure body 604 is made of a high permeability material, such as those previously described with respect to the magnet holder 104.

The knob 606 comprises a cylindrical portion (visible in FIG. 7) and an elongate portion (obscured from view in FIG. 7) extending outward from the cylindrical portion wherein the elongate portion of the knob 606 is externally threaded to mate with the internal threading of the magnet 102. The knob 606 is threaded into the magnet 102 and secured to a first end 614 of the enclosure body 604 in a known manner such that the knob 606 is free to rotate and is inhibited from axial translation with respect to the enclosure body 604. Thus, rotation of the knob 606 will induce the magnet 102 to extend and retract axially from the cavity 612 in response to actuation of the knob 606. The threading of the magnet 102 and the knob 606 is preferably of a rapid twist such that movement of the magnet 102 between the shielded 112 and exposed 114 configurations can be achieved by rotating the knob 606 no more than a full turn. FIG. 7 illustrates the magnet 102 in an intermediate position between the shielded 112 and the exposed 114 configurations.

The cap 610 is a hollow, cylindrical elongate member and is configured to friction fit with the exterior of the enclosure body 604 in a known manner. In one embodiment, the enclosure body 604 is of adequate size to effectively shield the magnet 102 in the shielded configuration 112 by itself. In this embodiment, the cap 610 is made of a less expensive material such as plastic. In an alternative embodiment, the cap 610 is also made of a high permeability material, such as those previously described with respect to the magnet holder 104. When positioned in friction fit with the enclosure body 604, the cap 610 acts in concert with the enclosure body 604 to shield the magnetic field developed by the magnet 102 in a similar manner to that previously described with respect to other embodiments of the shielded magnet assembly 100, 200, 300, 400, and 500. The cap 610 of both embodiments also obscures the magnet 102 from view and inhibits entrance of debris into the cavity 612.

Figure 8A:
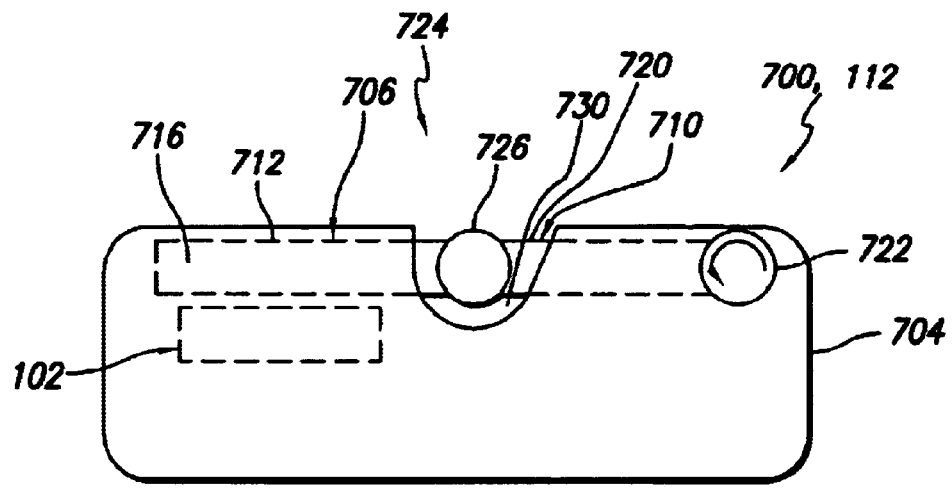
FIG. 8A illustrates one more embodiment of a shielded magnet assembly in a shielded configuration.
Figure 8B:
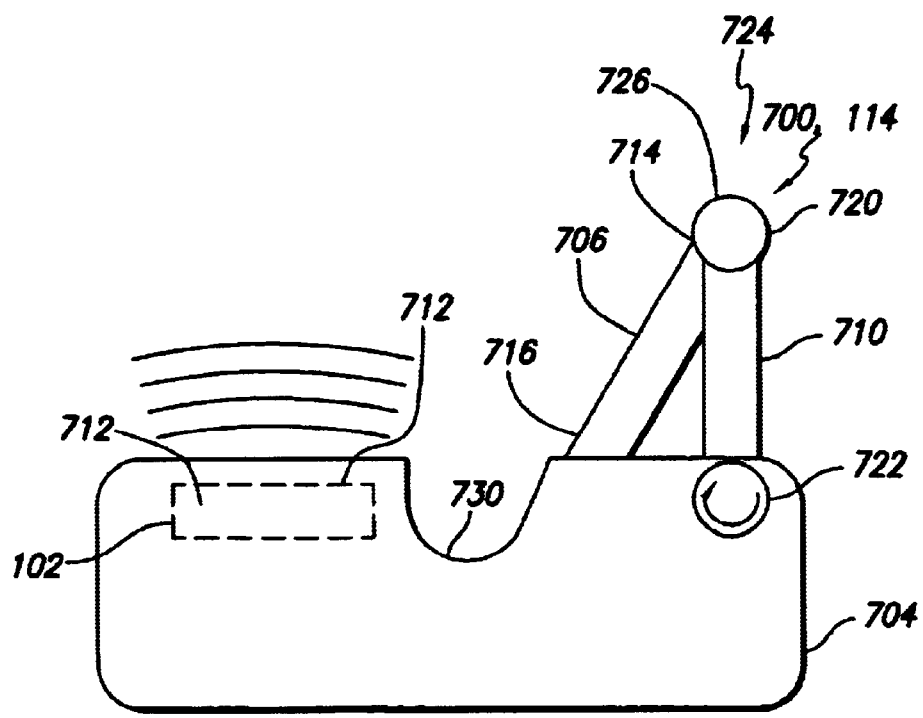
FIG. 8B illustrates the shielded magnet assembly of FIG. 8A in an exposed configuration.

FIG. 8 illustrates a further embodiment of a shielded magnet assembly 700 in the shielded 112 (FIG. 8A) and exposed 114 (FIG. 8B) configurations. The shielded magnet assembly 700, of this embodiment, comprises the magnet 102, an enclosure body 704, a shield cover 706, and a shield actuator 710. The enclosure body 704 and the shield cover 706 are made of a high permeability material, such as those previously described with respect to the magnet holder 104. The shield actuator 710 may be made of a high permeability material, such as those previously described with respect to the magnet holder 104, or other rigid material such as steel or plastic.

The enclosure body 704 is generally rectangular and defines a rectangular cavity 712 extending into one face of the enclosure body 704. The cavity 712 is sized and configured to securely retain the magnet 102 in a friction fit such that the magnet 102 is positioned at least 1 cm below the face of the enclosure body 704. The enclosure body 704 of this embodiment further defines a clearance groove 730 extending across the enclosure body 704, adjacent the cavity 712, approximately midway between opposite ends of the enclosure body 704. The clearance groove 730 provides clearance for a user to grasp the shield cover 706 and shield actuator 710.

The shield cover 706 and the shield actuator 710 are elongate, rigid members of approximately the same length. The shield cover 706 is hingedly attached at a first end 714 to a first end 720 of the shield actuator 710. A second end 722 of the shield actuator 710, opposite the first end 720, is hingedly attached to the enclosure body 704, thereby defining a toggle joint 724 structure of a type known in the art. A second end 716 of the shield cover 706 opposite the first end 714 is free to move. The hinged connection of the shield cover 706 to the shield actuator 710 defines a knurled gripping surface 726.

In the shielded configuration 112 as illustrated in FIG. 8A, the shield cover 706 and the shield actuator 710 are collinear and extend along the face of the enclosure body 704 with the cavity 712. The shield cover 706 is positioned and is of such a configuration as to substantially cover the magnet 102 positioned within the cavity 712. Thus, in the shielded configuration 112, the magnetic field developed by the magnet 102 is substantially directed within the shield cover 706 and the enclosure body 704. In one embodiment, the hinged connection of the shield actuator 710 to the enclosure body 704 includes a spring connected between the shield actuator 710 and the enclosure body 704 in a known manner so as to bias the shielded magnet assembly 700 in the shielded configuration 112.

Drawing the gripping surface 726 away from the enclosure body 704 will thus induce the shield actuator 710 to pivot about the second end 722 which is hingedly attached to the enclosure body 706. Drawing the gripping surface 726 away from the enclosure body 704 will further induce the shield cover 706 to pivot with respect to the shield actuator 710 and thus draw the shield cover 706 away from the cavity 712. Drawing the shield cover 706 away from the cavity 712 will thus expose the magnet 102 so as to achieve the exposed configuration 114.

Figure 9:
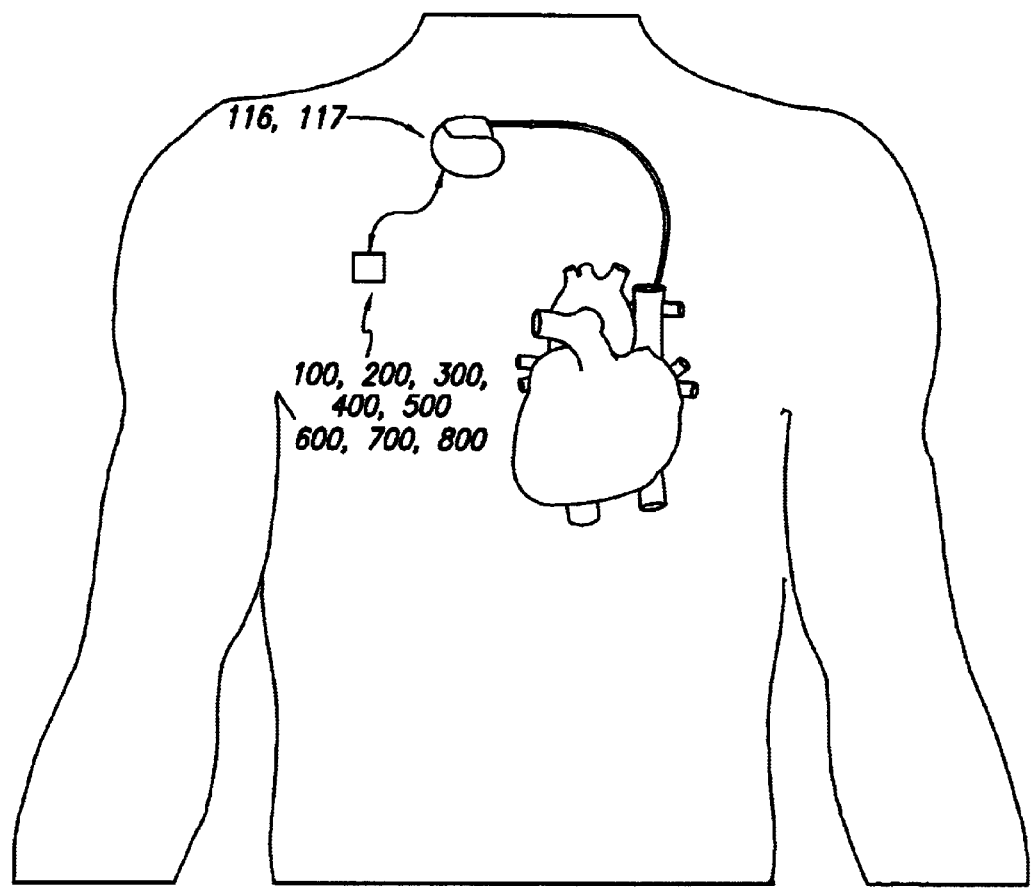
FIG. 9 illustrates a method of employing a shielded magnet assembly to selectively activate features of an implanted cardiac device.

FIG. 9 illustrates a method of selectively activating features of the implanted cardiac device 116. A user positions the assembly 100, 200, 300, 400, 500, 600, 700, or 800 adjacent the chest of the patient provided with the cardiac device 116. The user then manipulates the assembly 100, 200, 300, 400, 500, 600, or 700 to the exposed configuration 114 or activates the assembly 800 via a switch (not shown). The user then manipulates the assembly 100, 200, 300, 400, 500, 600, or 700 to the shielded configuration 112 or deactivates the assembly 800 via the switch (not shown) and distances the assembly 100, 200, 300, 400, 500, 600, 700, or 800 from the patient's chest.

As is schematically illustrated in FIG. 9, the implanted cardiac, stimulation device 116 includes at least one magnetic switch 117. The at least one magnetic switch 117 can be a well known Reed switch that is activated when exposed to a magnetic field having a threshold value. Activation of the Reed switch results in a microprocessor of the implanted cardiac stimulation device 116 initiating a function. One common function is the enabling of a telemetry circuit to permit RF transmission of data from the implanted device to an external programmer. The use of such Reed switches is preferred as it permits selective activation of a device function without requiring continuous consumption of power by the implanted device or an invasive procedure. The magnetic device of the illustrated embodiments is configured to be used with any magnetic switch, including Reed switches, known in the art without departing from the spirit of the present invention.

It should be appreciated that in the embodiments of the shielded magnet assemblies 100, 200, 300, 400, 500, 600, and 700 previously described, the orientation of the magnet 102 with respect to polarity in the exposed configuration 114 is not important to the use of the shielded magnet assemblies 100, 200, 300, 400, 500, 600, and 700. However, it should also be appreciated that in alternative embodiments wherein the polarity of the magnet 102 is important, it is well within the skill of a person of ordinary skill in the art to orient the magnet 102 in a particular fashion without detracting from the scope of the invention. Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. A magnet device for magnetically activating a magnetic switch in an implantable cardiac device, the magnet device comprising:
   a magnet that produces a magnetic field strength of a first strength sufficient to activate a magnetic switch in an implantable cardiac device; and
   a housing that defines a high magnetic permeability path, wherein the housing has both an open configuration and a closed configuration and the magnet resides in the housing such that when the housing is in the closed configuration, the magnetic flux produced by the magnet is directed into the high magnetic permeability path such that the resulting strength of the magnetic field outside of the housing is diminished from the first strength such that the magnetic field will not activate the magnetic switch in the implantable cardiac device and wherein, when the housing is in the open configuration, the magnet produces a magnetic field outside of the housing having the first strength;
   wherein the housing comprises a first and a second shell that engage with each other so as to define an interior cavity that contains the magnet in the closed configuration and are at least partially separable from each other in the open configuration; and
   wherein the magnet is removable from the cavity defined by the first and second shells in the open configuration.

2. A magnet device for magnetically activating a magnetic switch in an implantable cardiac device, the magnet device comprising:
   a magnet that produces a magnetic field strength of a first strength sufficient to activate a magnetic switch in an implantable cardiac device; and
   a housing that defines a high magnetic permeability path, wherein the housing has both an open configuration and a closed configuration and the magnet resides in the housing such that when the housing is in the closed configuration, the magnetic flux produced by the magnet is directed into the high magnetic permeability path such that the resulting strength of the magnetic field outside of the housing is diminished from the first strength such that the magnetic field will not activate the magnetic switch in the implantable cardiac device and wherein, when the housing is in the open configuration, the magnet produces a magnetic field outside of the housing having the first strength;
   wherein the housing includes a cover that defines the high permeability path and wherein the cover is at least partially removable in the open configuration so as to expose the magnet to thereby result in the magnet producing the magnetic field having the first strength.

3. The device of claim 2, wherein the high permeability path defined by the housing is formed of iron.

4. The device of claim 2, wherein the high permeability path defined by the housing is formed of an alloy comprising approximately 77% Nickel, 14% Iron, 5% Copper, and 4% Molybdenum.

5. The device of claim 2, wherein the magnet produces a magneto-static field of approximately at least 10 Gauss as measured approximately 7.6 cm from the permanent magnet.

6. The device of claim 2, wherein the magnetic field produced by the magnet, when the magnet is positioned within the housing and the housing is in the closed configuration, is less than approximately 2 Gauss as measured 7.6 cm from the magnet.

7. The device of claim 2 wherein the cover is hingeably attached to the housing.

8. The device of claim 2, wherein the magnet is fixedly attached to the housing.

9. The device of claim 8, further comprising an extension mechanism that interconnects the magnet to the container such that the magnet can be extended beyond the cavity of the housing to thereby produce the magnetic field having the first strength.

10. The device of claim 9, wherein the extension mechanism comprises a spring loaded extension mechanism.

11. The device of claim 9, wherein the extension mechanism comprises a screw mechanism such that rotation of a portion of the housing results in extension of the magnet such that the magnet protrudes out of the housing.

12. The device of claim 2, wherein the magnet device is sized to fit in the palm of an operator.

13. A portable magnet device for magnetically activating a magnetic switch in an implantable cardiac device, the magnet device comprising:
   magnetic means for producing a magnetic field of a first strength sufficient to activate the magnetic switch in an implantable cardiac device; and
   shielding means for selectively shielding the magnetic means such that the magnetic field produced by the magnetic means when shielded by the shielding means is diminished to below a first threshold to thereby reduce the likelihood that the magnetic means will damage other magnetic media while the magnet device is being carried by a treating physician;
   wherein the magnetic means when shielded by the shielding means is diminished to below the first threshold that the magnetic field will not activate the magnetic switch in the implantable cardiac device;
   wherein the shielding means comprises a housing that contains the permanent magnet;
   wherein the shielding means comprises a housing that contains the permanent magnet; and
   wherein the housing includes a cover that defines the high permeability path and wherein the cover is at least partially removable in the open configuration so as to expose the magnet to thereby result in the magnet producing the magnetic field having the first strength.

14. The device of claim 13, wherein the magnetic means comprises a permanent magnet that when not shielded by the shielding means produces a magnetic field of approximately 10 Gauss as measured approximately 7.6 cm from the magnet device.

15. The device of claim 13, wherein the magnetic device when in the shielded configuration produces a magnetic field of less than approximately 2 Gauss as measured approximately 7.6 cm from the magnetic device.

16. The device of claim 13, wherein the cover is hingeably attached to the housing.

17. The device of claim 13, wherein the magnet is fixedly attached to the housing.

18. The device of claim 17, further comprising an extension mechanism that interconnects the magnet to the container such that the magnet can be extended beyond the cavity of the housing to thereby produce the magnetic field having the first strength.

19. The device of claim 18, wherein the extension mechanism comprises a spring loaded extension mechanism.

20. The device of claim 18, wherein the extension mechanism comprises a screw mechanism such that rotation of a portion of the housing results in extension of the magnet such that the magnet protrudes out of the housing.

21. The device of claim 13, wherein the magnet means is sized to fit in the palm of the treating physician.

22. A portable magnet device for magnetically activating a magnetic switch in an implantable cardiac device, the magnet device comprising:

magnetic means for producing a magnetic field of a first strength sufficient to activate magnetic switch in an implantable cardiac device; and shielding means for selectively shielding the magnetic means such that the magnetic field produced by the magnetic means when shielded by the shielding means is diminished to below a first threshold to thereby reduce the likelihood that the magnetic means will damage other magnetic media while the magnet device is being carried by a treating physician;

wherein the magnetic means when shielded by the shielding means is diminished to below the first threshold that the magnetic field will not activate the magnetic switch in the implantable cardiac device;

wherein the shielding means comprises a high magnetic permeability structure that is positioned in proximity to the magnetic means such that a substantial portion of the magnetic flux produced by magnetic means is directed into a high magnetic permeability path defined by the high magnetic permeability structure;

wherein the shielding means comprises a housing that contains the permanent magnet;

wherein the housing comprises a first and a second shell that engage with each other so as to define an interior cavity that contains the magnet in a closed configuration and are at least partially separable from each other in an open configuration; and wherein the magnet is removable from the cavity defined by the first and second shells in the open configuration.

\* \* \* \* \*